United States Patent [19]
Chiesi et al.

[11] Patent Number: 6,114,391
[45] Date of Patent: Sep. 5, 2000

[54] α-AMINO ACID AMIDES, PREPARATION THEREOF AND THE THERAPEUTICAL USE THEREOF

[75] Inventors: Paolo Chiesi; Paolo Ventura; Maurizio Del Canale; Renato De Fanti; Elisabetta Armani; Gino Villetti; Claudio Pietra, all of Parma, Italy

[73] Assignee: Chiesi Farmaceutici S.p.A., Parma, Italy

[21] Appl. No.: 09/147,553

[22] PCT Filed: Jul. 15, 1997

[86] PCT No.: PCT/EP97/03773
§ 371 Date: Feb. 19, 1999
§ 102(e) Date: Feb. 19, 1999

[87] PCT Pub. No.: WO98/03472
PCT Pub. Date: Jan. 29, 1998

[30]  Foreign Application Priority Data

Jul. 23, 1996 [IT] Italy .................. MI96A1544

[51] Int. Cl.$^7$ ........................ A61K 31/165; C07C 233/05
[52] U.S. Cl. ................ 514/619; 514/617; 514/620; 564/142; 564/164; 564/165; 564/193; 564/197
[58] Field of Search ..................... 514/619, 620, 514/617; 564/142, 164, 165, 193, 197

[56]  References Cited

U.S. PATENT DOCUMENTS 5,198,547  3/1993  Bailey et al. .......................... 544/258

FOREIGN PATENT DOCUMENTS 0 333 154   9/1989   European Pat. Off. .
0 400 495  12/1990   European Pat. Off. .
2 048 852  12/1980   United Kingdom .

OTHER PUBLICATIONS

Altamura et al, J. Med. Chem, vol. 38, pp. 4244–4256, 1995.

Pevarello et al, The New Journal of Organic Synthesis, pp. 179–183, 1996.

*Primary Examiner*—Shailendra Kumar
*Attorney, Agent, or Firm*—Oblon, Spivak, McClelland, Maier & Neustadt, P.C.

[57]  ABSTRACT

The present invention relates to serinamide, glycinamide, alaninamide and phenylalaninamide derivatives of formula (I) wherein R, R', $R_1$ and $R_2$ are as defined in the disclosure. The compounds (I) are useful for the treatment of neurological diseases.

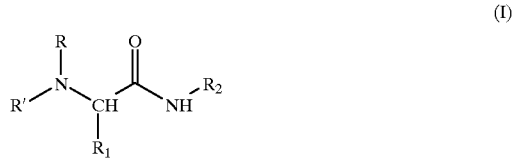

(I)

14 Claims, No Drawings

α-AMINO ACID AMIDES, PREPARATION THEREOF AND THE THERAPEUTICAL USE THEREOF

This application is a 371 of PCT/EP97/03773, filed Jul. 15, 1997.

The present invention relates to α-amino acid amides, processes for the preparation thereof and pharmaceutical compositions containing them.

More precisely, the invention relates to serinamide, glycinamide alaninamide and phenylalaninamide derivatives of general fonmula (I):

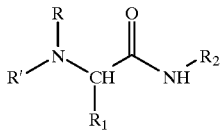

wherein

R is a straight or branched alkyl cycloalkyl; arylalkyl or phenylalkyl optionally substituted at the ring with alkyl, halogen or haloalkyl; fused or non-fused aryl optionally substituted with alkyl, alkoxy, halogen or haloalkyl;

R' is hydrogen; alkyl; phenyl; phenylalkyl;

$R_1$ is optionally acylated $C_1$–$C_4$ hydroxyalkyl or phenylalkyl, when R is alkyl, cycloalkyl, arylalkyl; or $R_1$ is hydrogen, $C_1$–$C_4$ alkyl, optionally acylated $C_1$–$C_4$ hydroxyalkyl or phenylalkyl when R is aryl $R_2$ is hydrogen; alkyl; phenyl; phenylalkyl.

An alkyl group if not otherwise specified is preferably a $C_1$–$C_{10}$ alkyl group such as methyl, ethyl, n-propyl, isopropyl, n-butyl, isobutyl, n-pentyl, n-hexyl, n-heptyl, n-octyl, n-nonyl, 2-ethylpentyl, 1-ethylheptyl, 1-methyloctyl, 4-heptyl.

A cycloalkylalkyl group is preferably a group having 1 to 3 carbon atoms in the alkyl moiety and 3 to 7 carbon atoms in the cycloalkyl moiety such as cyclopropylmethyl, cyclopentylmethyl, cyclohexylmethyl, 1-(5-norbornylenyl) ethyl.

An optionally substituted arylalkyl or phenylalkyl group is preferably 2-naphthalenylmethyl, benzyl, phenethyl, phenylpropyl, phenylbutyl, 3-(4-methylphenyl)propyl, 3-(4-fluorophenyl)propyl, 3-(4-chlorophenyl)propyl, 3-(4-trifluoromethylphenyl)propyl, 3-phenyl-1-methylpropyl, 2-phenyl-1-methylethyl, 3-phenyl-3-methyl-propyl, 1-phenylethyl.

A fused or non-fused aryl group is preferably 1,2,3,4-tetrahydro-2-naphthalenyl, 2-indanyl optionally substituted by one or more alkoxy, halogen or haloalkyl groups.

An acylated $C_1$–$C_4$ hydroxyalkyl group is preferably acetoxyalkyl, propanoyloxyalkyl, 2-methylpropanoyloxyalkyl, benzoyloxyalkyl group.

A class of preferred compounds is that wherein:

$R_1$ is $CH_2OH$; R is $C_3$–$C_{10}$ alkyl, $C_2$–$C_4$ phenylalkyl, 1,2,3,4-tetrahydro-2-naphthalenyl or 2-indanyl optionally substituted with alkyl, alkoxy, halogen or haloalkyl; R' is hydrogen or methyl and $R_2$ is hydrogen or methyl.

A particularly preferred sub-class is that wherein $R_1$ is $CH_2OH$; R is phenyl-($C_2$–$C_3$)-alkyl or 1,2,3,4-tetrahydro-2-naphthalenyl, or 2-indanyl optionally substituted by one or more alkoxy, halogen, haloalkyl groups; R' and $R_2$ are hydrogen.

A second class of preferred compounds is that wherein $R_1$ is hydrogen or methyl, R is 1,2,3,4-tetrahydro-2-naphthalenyl or 2-indanyl optionally substituted by one or more alkoxy, halogen, haloalkyl groups and R' and $R_2$ are hydrogen.

The compounds of the invention can be in the form of organic or inorganic acid addition salts.

Moreover they can have one or more asymmetric carbon atoms, therefore they can be used both in the form of mixtures containing more diastereoisomers in any ratio, and in the form of racemic mixtures containing couples of enantiomers in equal or different ratios, and in the form of optically pure compounds.

The compounds of the invention can be used in the treatment of chronic neurodegenerative diseases, such as Alzheimer's disease, various forms of dementia, Parkinson's disease, Huntingdon's disease or acute neurodegenerative impairments such as stroke and head injuries; in the treatment of epilepsy and depression.

PRIOR ART

GB patent 2048852 (Continental Pharma S.A.) discloses 2-aminoacetamide (commonly referred to as glycinamide) derivatives which can be used in the treatment of epilepsy, in the treatment of dyskinesias such as Parkinsons's disease, in the treatment of memory disorders and possibly in the treatment of depression.

Some of the disclosed compounds, orally administered in doses of 10–100 mg/kg, showed anticonvulsive effects against bicuculline-induced tonic convulsions in mouse.

2-n-Pentylaminoacetamide (in the following referred to with the nonproprietary name milacemide) and its hydrochloride were particularly studied.

Milacemide was used as the reference compound to test the pharmacological activity of the compounds of the present invention.

EP-B1-0400495 (Farmitalia Carlo Erba) discloses α-aminocarboxamide N-phenylalkyl substituted derivatives.

Examples of particularly preferred compounds are aminopropionamide (particularly alaninamide and serinamide) and aminoacetamide(glycinamide)N-phenylalkyl substituted derivatives. Said compounds are active on Central Nervous System and can be used as antiepileptics, anti-Parkinsons, antineurodegeneratives, antidepressants, hypnotics and antispastics.

The activity of the compounds has been evaluated in the mouse as the anticonvulsive action against bicuculline- or 3-mercaptopropionic acid-induced convulsions.

The compounds described in EP-B1-0400495 are also potent monoamino oxidase (MAO) inhibitors.

WO 94/22808 and WO 94/22809 (Pharmacia/Farmitalia Carlo Erba) disclose other aminopropionamide derivatives, acting on Central Nervous System, respectively arylalkoxybenzyl- and arylalkylaminobenzyl-substituted.

One of the most representative compounds of the invention in WO 94/22808 is FCE28245, chemically 2-{4-[3-phenylpropyl]oxybenzyl]-amino-3-hydroxypropanamide methanesulfonate claimed to be active in the test of the electro-shock convulsions in the mouse.

PCT n° WO 95/18617 (Teva-Technion) and PCT n. WO 96/21640 (Teva-Lemmon) describe 1-aminobenzocycloalkane derivatives, such as 1-aminoindans and 1-aminotetralins, which can be used in the treatment of Parkinson's diseases, dementias, epilepsy and in post-traumatic diseases.

However, some of the described compounds, such as racemic N-(2-acetamido)-1-aminoindan and its optically active forms; N-(2-acetamido)-6-fluoro-1-aminoindan;

N-(2-acetamido)-1-aminotetralin; N,N-di-(2-acetamido)-1-aminoindan and N-(2-propionamido)-1-aminoindan were not very effective in the anticonvulsant activity test and don't seem endowed with a particularly favorable therapeutic index.

Now it has been found that cc-amino acids amides of general formula (I) are characterized by a higher efficacy and/or a better pharmacological profile than the prior art compounds.

The compounds of the invention can be prepared reacting amino acids esters or amides of formula II

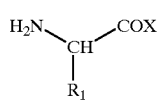

(II)

wherein R, is as defined above and X is an alkoxy group, a $NH_2$ group, or a $NH—R_2$ group wherein $R_2$ is as defined above, with compounds of formula III

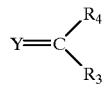

(III)

wherein Y is an oxygen atom or a NH group, whereas $R_3$ and $R_4$, which are the same or different, are hydrogen or, together with the carbon atom they are linked to, they form one of the groups R or R', except for non-fused aryl, as defined above, to give compounds of formula IV

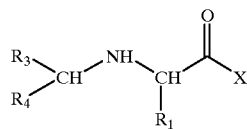

(IV)

which can then be transformed into compounds of formula I by means of one or more of the following reactions:
  when X is an alkoxy group, reaction with an amine of formula $R_2—NH_2$;
  N-alkylation;
  acylation of any hydroxy group present in $R_1$;
  salification and/or optical resolution.
  elimination of any protecting groups.

A first embodiment of the process described above involves the reductive amination of a compound of formula II or a salt thereof (generally the hydrochloride) wherein X is an alkoxy group, for example methoxy, with a compound of general formula III wherein Y is oxygen and the subsequent reaction with an amine of formula $R_2—NH_2$, The reductive amination is carried out according to conventional methods, using stoichiometric amounts or slight excesses of the reagents, at temperatures ranging from 0 to 40° C. and in organic solvents such as alcohols or acetonitrile. A hydride such as sodium cyanoborohydride or hydrogen in the presence of a catalyst such as Pd on-carbon can be used as a reducing agent.

The subsequent amidation reaction is carried out using an amine excess in water or in an organic solvent, particularly methanol or ethanol, at room temperature or heating in a chemical reactor.

A second embodiment involves the reductive amination of a compound II wherein X is a $R_2—NH$ group, according to the procedures already described.

Finally, a third embodiment involves the transimination of a compound II wherein X is $R_2—NH—$ with an imine compound (generally a phenylimine) III wherein Y is NH. The reaction is carried out in an organic solvent, for example an alcohol, methylene chloride or acetonitrile at a temperature from 0° to 40° C. The subsequent reduction of the resulting compound is carried out in an organic solvent, generally an alcohol such as ethanol or methanol, using a hydride such as sodium borohydride as reducing agent, at a temperature from 0° to 40° C.

Alternatively, the compounds I can also be prepared by condensation of an alfa-halogen ester of formula V

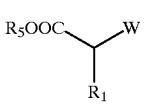

(V)

wherein $R_1$ is as defined above and preferably H, W is a halogen atom (generally chlorine or bromine) and $R_5$ is an alkyl group, with an amine of formula VI

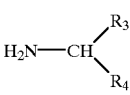

(VI)

wherein $R_3$ and $R_4$ are as defined above, and subsequent amidation with the amine $R_2—NH_2$. The condensation of compound V with compound VI is carried out in an organic solvent, for example acetonitrile, alcohol, dimethylformamide at a temperature from 40° to 140° C. in the presence of an acid-binding agent, for example potassium carbonate and preferably in the presence of catalytic amounts of potassium iodide. The amidation is then carried out as described above.

It is also possible to condense an alfa-halogen amide with the amine VI.

For the envisaged therapeutical uses, compounds I will be formulated in suitable pharmaceutical compositions which are a further object of the invention.

Said compositions will typically contain 1 to 1000 mg of active ingredient, particularly 10 to 100 mg, and will be administered one or more times a day depending on the disease, the pharmacokinetics of the selected active ingredient and the conditions (weight, sex, age) of the patient.

The compositions will be prepared using conventional techniques and excipients as described for example in Remington's Pharmaceutical Sciences Handbook, Mack. Pub., N.Y., U.S.A., and will be administered by the oral, parenteral or rectal route. Examples of formulations comprise tablets, capsules, syrups, granulates, sterile injectable solutions or suspensions, suppositories and the like.

The following examples further illustrate the invention.

EXAMPLES

Example 1 a) Preparation of N-(3-phenylpropyl)-L-serine methyl ester hydrochloride

L-Serine methyl ester hydrochloride (0.9 moles, 14 g), triethylamine (0.9 moles, 9.1 g) and 3-phenylpropionaldehyde (0.9 moles, 12.1 g) are dissolved in dry methanol (370 ml) in a Parr bottle and hydrogenated under 45 psi in the presence of 10% Pd/C, until the hydrogen absorption ceases.

The catalyst is filtered off and the filtrate is evaporated to dryness under vacuum. The resulting oil is taken up with methylene chloride (500 ml), the organic solution is washed with water and evaporated to dryness under vacuum to obtain a pale yellow oil.

The product is recovered as the hydrochloride by dissolution in ethyl ether (800 ml) and acidification with methanol hydrochloric acid. The precipitate is filtered and dried under vacuum at 45° C. Yield: 17.5 g (71%)—m.p.= 126–129° C.

b) Preparation of (−)-(S)-3-hydroxy-2-(3-phenylpropylamino)propanamide hydrochloride (CHF 2803.01)

The product obtained in a)! (0.06 moles, 17 g) is dissolved in water (500 ml) and alkalinized with 10% aqueous potassium carbonate to pH=8. The free base is extracted with methylene chloride and evaporated to dryness under vacuum. The resulting pale yellow oil (16.3 g) is dissolved in methanol (150 ml). Ammonia is bubbled through the solution, cooled at −5° C., to a ~15M concentration. The hermetically sealed system is reacted for 5 days at room temperature (r.t.), then evaporated to dryness under vacuum. The product is recovered as the hydrochloride by dissolution in ethanol (40 ml), acidification with ether HCl and precipitation with ethyl ether (500 ml).

The white solid is filtered and dried under vacuum at 40° C. Yield: 7.6 (46.5%)—m.p.: 153–155° C. $[\alpha]^{589}$ (c=1, methanol)=−13.5

Example 2 a) Preparation of N-(2-tetralyl)-D-serine methyl ester

Sodium cyanoborohydride (0.07 moles, 4.5 g) is added to a solution of β-tetralone (0.068 moles, 10.5 g) and D-serine methyl ester hydrochloride (0.07 moles, 11 g) in 10/1 ethanol/methanol (550 ml). The mixture is reacted at r.t. for 24 hours, evaporated to dryness under vacuum, taken up with water (800 ml) and extracted with ethyl acetate (2×500 ml). The combined organic phases are extracted with 1N HCl (2×300 ml). The aqueous phases are alkalinized with sodium bicarbonate and extracted with ethyl acetate (3×200 ml). The combined organic phases are evaporated to dryness under vacuum, to yield the product as a yellow oil. Yield: 12 g (72%)

b) Preparation of (R)-3-hydroxy-2-(1,2,3,4-tetrahydronaphthalen-2-(R,S)-ylamino)propanamide (CHF 2818)

Ammonia is bubbled through a solution of N-(2-tetralyl)-D-serine methyl ester (0.048 moles, 12 g) in methanol (150 ml), at 0° C., to a ~15M concentration. The hermetically sealed system is reacted at r.t. for 120 hours. The solution is evaporated to dryness under vacuum and the residual oil solidifies upon grinding in petroleum ether. Yield: 9 g (80%)—m.p.: 104–115° C.

c) Separation of CHF 2818 diastereomers Preparation of 3-hydroxy-2-(R)-(1,2,3,4-tetrahydro-naphthalen-2-(S)ylamino)propanamide (CHF 2983)

2-(R)-(1,2,3,4-Tetrahydro-2-(R,S)-naphthalenylamino)-3-hydroxypiopanamide (0.038 moles, 8.8 g) is crystallized in ethyl acetate (200 ml) and the resulting solid is recrystallized in ethyl acetate (200 ml) twice and finally in ethanol (50 ml). The crystalline white solid is dried under vacuum at 45° C. Yield: 1.9 g (yield 43%)—m.p.=142–145° C. $[\alpha]^{589}$ (c=1, methanol)=+92 d) Preparation of 3-hydroxy-2-(R)-(1,2,3,4-tetrahydronaphthalen-2-(R)ylamino)propanamide hydrochloride (CHF 2982.01).

The mother liquors from the first three crystallizations of CHF 2983 are combined and left at 0° C. for 48 hours: the precipitate is filtered off and the filtrate is evaporated to dryness under vacuum. The resulting wax solidifies by trituration in ethyl ether (50 ml) at r.t.

The solid is recovered as the hydrochloride by dissolution in methanol HCl (3M, 20 ml) and evaporation to dryness under vacuum, then crystallized from 1/1 ethanol/ethyl acetate (400 ml). The crystalline white solid is dried under vacuum at 45° C. Yield: 1.8 g (36 %)—m.p.=226–232° C. $[\alpha]^{589}$ (c=1, methanol)=−105.1

Example 3 a) Preparation of 3-(4-methylphenyl)propanoyl chloride 3-(4-Methylphenyl)propanoic acid (0.055 moles, 9 g) is dissolved in thionyl chloride (1.008 moles, 120 g). The mixture is stirred for 30' at r.t., then refluxed for 1 h 30', evaporated under vacuum to an oil and taken up with toluene and hexane, each time evaporating to dryness. Yield: 12.4 g b) Preparation of 3-(4-methylphenyl)propanal A solution of triphenylphosphine (0.117 moles, 30.8 g) in acetone (200 ml) is added under a nitrogen stream at r.t. with Cu (I) bis-(triphenyl-phosphine)-tetrahydroborate (0.067 moles, 40.69 g), then 3-(4-methylphenyl)propanoyl chloride (0.055 moles, 10 g) dissolved in acetone (85 ml) is dropped in 45'. The mixture is stirred at r.t. under nitrogen for 1 h. The precipitated solid is filtered, washing with acetone and the filtrate is evaporated under vacuum. The residue is dissolved in chloroform (340 ml), added with cuprous chloride (0.135 moles, 13.38 g) and stirred under nitrogen stream for 1 h at r.t. The mixture is filtered through celite, the filtrate is evaporated to dryness and the resulting residue is taken up into ethyl ether and petroleum ether, filtered and evaporated under vacuum to obtain an oil. Yield: 6.7 g (83%)

c) Preparation of 3-hydroxy-2-(3-(4-methylphenyl)propylamino)propanoic acid methyl ester hydrochloride 2% Sodium in methanol (0.045 moles, 51.7 ml) is added to D,L-Serine methyl ester hydrochloride (0.045 moles, 7 g), dissolved in methanol (70 ml), to obtain the free base.

The formed sodium chloride is precipitated with ethyl ether (150 ml) and filtered off. The filtrate is evaporated to dryness under vacuum. The resulting residue is dissolved in methanol (450 ml), added with 3-(4-methylphenylpropanal) (0.045 moles, 6.7 g) and adjusted to pH 6 with acetic acid, sodium cyanoborohydride (0.048 moles, 3 g) is added and the mixture is reacted at r.t. for 24 hours. The mixture is acidified with methanol HCl, evaporated to dryness under vacuum, taken up with methylene chloride (600 ml), then alkalinized with triethylamine and washed with water (3×500 ml). The organic phase is evaporated to dryness under vacuum and the product is recovered as the hydrochloride taking up with ethyl ether (400 ml) and acidifying with ether HCl. The precipitated white solid is dried under vacuum at 30° C. Yield: 8.8 g (68%)

d) Preparation of 3-hydroxy-2-(3-(4-methylphenyl)propylamino)propanamide hydrochloride (CHF 2934.01)

3-Hydroxy-2-(3-(4-methylphenyl)propylamino) propanoic acid methyl ester hydrochloride (0.03 moles, 8,6 g) is dissolved in water (500 ml), alkalinized with 10% aqueous potassium carbonate to pH=8. The free base is extracted with methylene chloride and evaporated to dryness under vacuum. The resulting pale yellow oil (16.3 g) is dissolved in methanol (150 ml). Ammonia is bubbled through the solution, cooled at −5° C., to a ~15M concentration. The hermetically sealed system is reacted for 5 days at r.t., then evaporated to dryness under vacuum. The product is recovered as the hydrochloride by dissolution in ethanol (40 ml), acidification with ether HCl and precipitation with ethyl ether (500 ml). The white solid is filtered and dried under vacuum at 40° C. Yield: 4.9 g (60 %)—m.p.= 173–176° C.

Example 4
a) Preparation of 4-phenylbutanoyl chloride

4-Phenyl-butanoic acid (0.83 moles, 13.57 g) is added to thionyl chloride (0.114 moles, 8.27 ml) and warmed to dissolve the solid. The mixture is stirred for 30' at r.t., then refluxed for 10', finally recovered as in example 3a). A 100% yield is obtained (0.083 moles, 15.09 g).

b) Preparation of 4-phenylbutanal

The procedure as in 3b) is followed, starting from 4-phenylbutanoyl chloride (0.083 moles, 15.09 g), to obtain 11 g of product.

c) Preparation of (R)-3-hydroxy-2-(4-phenylbutylamino) propanoic acid methyl ester hydrochloride 2% Sodium in methanol (0.052 moles, 59.8 ml) is added to D-Serine methyl ester hydrochloride (0.052 moles, 8.16 g), dissolved in methanol (81.6 ml), to release the base. The formed sodium chloride is precipitated with ethyl ether (163 ml) and filtered off. The filtrate is evaporated to dryness under vacuum. The resulting residue is dissolved in methanol (150 ml), added with 4-phenylbutanal (0.051 moles, 10.69 g) and adjusted to pH 6 with acetic acid, added with sodium cyanoborohydride (0.055 moles, 3.62 g) and reacted at r.t. for 24 hours. The mixture is acidified with methanol HCl, evaporated to dryness under vacuum, taken up in methylene chloride (600 ml) and in a 1M sodium bicarbonate solution. The phases are separated and the aqueous one is extracted again with methylene chloride (3×200 ml), then the combined organic phases are washed with water and evaporated to dryness under vacuum. The product is recovered as the hydrochloride, taking up with ethyl ether (180 ml) and acidifying with ether HCl. The precipitated white solid is dried under vacuum at 30° C. Yield: 5.83 g (40%)

d) Preparation of (R)-3-hydroxy-2-(4-phenyl)butylamino) propanamide (CHF 2918)

(R)-3-(Hydroxy-2-(4-phenylbutylamino)propanoic acid methyl ester hydrochloride (0.02 moles, 5.83 g) is dissolved in water (250 ml) and alkalinized with 10% aqueous sodium carbonate. The free base is extracted with methylene chloride (3×200 ml) and evaporated to dryness under vacuum. The resulting pale yellow oil is dissolved in methanol (150 ml). Ammonia is bubbled through the solution, cooled at −5° C., to a ~15M concentration. The hermetically sealed system is reacted for 5 days at r.t., then evaporated to dryness under vacuum to obtain a thick oil. The product is obtained as a solid taking up with ethyl ether (25 ml) and precipitating with hexane (400 ml). The white solid is filtered and dried under vacuum at 35° C. Yield: 4.43 g (92 %)—m.p.=59–61° C.

With similar procedures as described in the examples 1 to 4 th compounds 1 to 5, 27, 28, 30, 33, 34, 38, 39, 42 to 44, 46 to 48, 52 and 53 of Table 1 were prepared.

Example 5
Preparation of (R)-3-hydroxy-2-(3-phenylpropylamino) propanamide (CHF 2679)

D-Serinamide (0.038 moles, 4 g) and 3-phenylpropanal (0.038 moles, 5.1 g) are dissolved in methanol (400 ml) in a Parr bottle and hydrogenated in the presence of 10% Pd/C (3 g) at 40 psi, until hydrogen absorption ceases. The catalyst is filtered off and the solution is evaporated to dryness under vacuum, taken up in ethyl acetate (300 ml) and washed with water (2×200 ml). The organic phase is dried and dissolved in warm ethyl ether (300 ml) to precipitate the product as a white solid by slow evaporation of the solvent at r.t. Yield: 3.8 g (45%)—m.p.=76–78° C. $[\alpha]^{589}$ (c=1, methanol)=+13.2°

With similar procedures as described in the example 5 the compounds 6 to 13, 15 to 22, 24, 26, 49 to 51 of Table 1 were prepared.

Example 6
Preparation of (R)-2-(4-heptylamino)-3-hydroxypropanamide phosphate (CHF 2870.02)

A solution of D-serinamide (0.01 moles, 1 g) and 4-heptanone (0.01 moles, 1.1 g) in methanol (50 ml) is added with 4M methanol HCl (0.0033 moles, 0.85 ml) and sodium cyanoborohydride (0.005 moles, 0.33 g). The mixture is reacted at r.t. for 10 days, acidified with methanol HCl to pH=2, and evaporated to dryness under vacuum. The residue is taken up with water (100 ml), washed with ethyl ether (100 ml), alkalinized with sodium carbonate and extracted with chloroform (3×100 ml). The resulting oil (1.3 g) is dissolved in methanol (50 ml) and treated with 85% phosphoric acid (0.0065 moles, 0.75 g), then evaporated to dryness under vacuum to obtain the product as a very light solid foam. Yield: 2 g (77%)—m.p.=150–156° C. $]^{589}$ (c=1, water)=+1.9

Example 7
a) Preparation of 3-hydroxy-2-(N-methyl-(3-phenylpropyl) amino)propanoic acid methyl ester A solution of N-(3-phenylpropyl)serine methyl ester (6.4 g, 0.027 mol) in methanol (150 ml) is added with 10% Pd-on-carbon (0.7 g) and 40% formic aldehyde (3.0 ml 0.04 mol) dissolved in methanol (50 ml). The mixture is stirred at room temperature under hydrogen atmosphere, under a slight pressure (40 psi) until the absorption ceases. The mixture is filtered and the filtrate is evaporated under vacuum. The residue is taken up in ethyl ether (300 ml), washed with water (2×200 ml), dried over sodium sulfate and evaporated under vacuum. Yield: 6.6 g b) Preparation of 3-hydroxy-2-(N-methyl-3-phenylpropyl) amino propanamide hydrochloride (CHF 2968.01)

The procedure of Example 3b is repeated.

Ammonia is bubbled through a solution of 3-hydroxy-2-(N-methyl-(3-phenylpropylamino)propanoic acid methyl ester (0.026 moles, 6.6 g) in methanol (150 ml), at 0° C., to a ~15M concentration. The system is reacted at T~80° C. for 120 hours in a closed reactor. The solution is evaporated to dryness under vacuum to obtain an oil from which the product is separated by low pressure liquid chromatography. The resulting oil is taken up in absolute ethanol and ethyl acetate, then acidified with ether HCl. The mixture is stirred, adding ethyl ether, then the precipitate is filtered and dried under vacuum at 40° C. Yield: 3.5 g.—m.p. 112–114° C.

With a similar procedure as described in the example 7 the following compounds were prepared: (R)-3-hydroxy-2-(N-methyl-2-indanylamino)propanamide hydrochloride (CHF 3440.01; compound n. 63) (S)-3-hydroxy-2-(N-methyl-2-indanylamino)propanamide hydrochloride (CHF 3462.01; compound n. 67).

Example 8
a) Preparation of methyl 2-(indanylamino)acetate

Glycine methyl ester (0.053 moles, 6.64 g) is dissolved in absolute ethanol (420 ml) and methanol (42 ml), added with 2-indanone (0.053 moles, 7 g), and with sodium cyanoborohydride (0.058 moles, 3.7 g) under stirring, in 40 minutes. The mixture is left under stirring at r.t. overnight, evaporated to dryness under vacuum and the residue is taken up with water (500 ml) and ethyl acetate (500 ml). The phases are separated and the organic phase is extracted with a 0.1N HCl solution (3×200 ml). The acidic solution is adjusted to pH 8.5–9 with a sodium bicarbonate saturated solution and extracted with ethyl acetate (3×250 ml). The organic solution is separated, dried over sodium sulfate and evaporated under vacuum. The resulting product is dried under vacuum at r.t. Yield: 5.8 g (53.4%)

b) Preparation of 2-(2-indanylamino)acetamide hydrochloride (CHF 3381.01)

Methyl 2-(indanylamino)acetate (0.028 moles, 5.8 g) is dissolved in ~15M ammonia in methanol (150 ml) and kept in a closed test tube at r.t. for some days. The 30 solution is evaporated to dryness under vacuum, taken up with absolute ethanol (2×200 ml) and evaporated each time. The oil is taken up into methanol (30 ml) and acidified to acid pH with a HCl solution in dry methanol under stirring. The product is precipitated by addition of ethyl ether, filtered and dried under vacuum at 45° C. Yield: 6.05 g (94.6%)—m.p.= 212–213° C.

Example 9
Preparation of 2-(N-methyl-2-indanylamino)acetamide (CHF 3488)

2-(2-indanylamino)acetamide (0.016 moles, 3.00 g) is dissolved in methanol (60 ml), and potassium carbonate (0.016 moles, 2.18 g) is added under stirring. Methyl iodide (0.028 moles, 4.14 g) is dropped therein at r.t. in 15 minutes. The mixture is reacted for 4 hours at r.t., then evaporated under vacuum. The resulting solid is taken up into water (100 ml), the aqueous solution is extracted with ethyl acetate (3×150 ml). The organic solution is dried over sodium sulfate, then evaporated under vacuum to obtain an oil which is chromatographed under medium pressure through silica gel (eluent chloroform:methanol=90:10) Yield: 1.31 g (40%)—m.p.=122–123° C.

Example 10
a) Preparation of methyl (S)-3-hydroxy-2-(2-indanylamino) propanoate

L-serine methyl ester hydrochloride (0.05 moles, 7.78 g) is dissolved in absolute ethanol (400 ml) and methanol (40 ml), added with 2-indanone (0.05 moles, 6.74 g) and sodium cyanoborohydride (0.55 moles, 3.64 g) under stirring in 30 minutes. The mixture is stirred at r.t. for 5 hours, then evaporated to dryness under vacuum and the residue is taken up into water (150 ml) and ethyl acetate (150 ml). The phases are separated and the aqueous phase is further extracted with ethyl acetate (200 ml). The combined organic phases are extracted with a 0.2 N HCl solution (2×200 ml). The aqueous solution is separated, adjusted to pH=8 with sodium bicarbonate and extracted with ethyl acetate (2×300 ml). The organic solution is separated, dried over sodium sulfate and evaporated under vacuum. The resulting product is dried under vacuum at r.t. Yield: 8.4 g (71.4%)

b) Preparation of (S)-3-hydroxy-2-(2-indanylamino) propanamide hydrochloride (CHF 2993.013

Methyl (S)-3-hydroxy-2-(2-indanylamino)propanoate (0.0357 moles, 8.4 g) is dissolved in ~12M ammonia methanol (150 ml) and kept in a closed test tube at r.t. for some days. The solution is evaporated to dryness under vacuum to obtain an oil which is taken up into methanol (2×250 ml), evaporating to dryness each time. The resulting product (base) is taken up into ethyl acetate (170 ml) and acidified to acid pH with a HCl solution in 4.75N dry ethyl acetate, under stirring. The product is filtered, crystallized from absolute ethanol and dried under vacuum at 40° C. Yield: 6.7 g (72.8%)—m.p.=186–187° C. $[\alpha]^{589}$ (c=1, methanol)=+16.6 (hydrochloride) $[\alpha]^{589}$ (c=1, methanol)=−24.6 (base)

With methods known in the art the mesylate salt (CHF 2993.02) was obtained. m.p. 180–183° C. $[\alpha]^{589}$ (c=1, methanol)=+13.4

With a similar procedure as described in the example 10 the compounds 41, 57, 61, 62, 69, 72, 75 and 76 of Table 1 were prepared.

Example 11
Preparation of (S)-2-(2-indanylamino)-3-(2-methylpropanoyloxy) propanamide hydrochloride (CEF 3542,01)

(S)-3-hydroxy-2-(2-indanylamino)-propanamide hydrochloride (CHF 2993.01, 0.006 moles, 1.6 g) is dissolved in trifluoroacetic acid (3.75 ml) and added with 2-methylpropanoyl chloride (0.022 moles, 2.3 ml) by dropping. After 2 hours at r.t. the solution is evaporated under vacuum and the resulting oil is taken up into ethyl ether (100 ml). The product is filtered, ground in ethyl ether (50 ml) and recovered by filtration. The solid is dried under vacuum at r.t. Yield: 1.8 g (90%)—m.p.=171–174° C.

With a similar procedure as described in the example 11 the following compounds were prepared: (S)-3-acetyloxy-2-(3-phenylpropylamino)propanamide hydrochloride (CHF 3023.01; compound n. 45); (S)-3-acetyloxy-2-(2-indanylamino)propanamide hydrochloride (CHF 3519.01; compound n. 74); $[\alpha]^{589}$ (c=1, methanol)=+29.8 (S)-3-benzoyloxy-2-(2-indanylamino)propanamide hydrochloride (CHF 3548.01; compound n. 78)

Example 12
Preparation of (S)-3-hydroxy-2-(2-indanylamino)-N-methylpropanamide hydrochloride (CHF 3422.01)

N-(2-indanyl)-(S)-serine methyl ester (0.025 moles, 5.95 g) is dissolved in 8.03M methylamine solution in ethanol (155 ml) in a closed test tube. After 1 day the solution is evaporated under vacuum taking up the resulting oil with methanol (3×100 ml), petroleum ether (fract. 40–70, 100 ml) and evaporating each time. The resulting oil, taken up with petroleum ether (250 ml), solidifies under stirring. The filtered solid (~5.42 g) is dissolved in lukewarm ethyl acetate (250 ml) and added with HCl in dry ethyl acetate (3.5 M) under stirring until markedly acid pH. The product is filtered, washed repeatedly with ethyl ether (150 ml) and dried in oven under vacuum. Yield: 5.33 g (77.9%)—m.p.= 190.5–192° C. $[\alpha]^{589}$ (c=1, DMSO)=+18 $[\alpha]^{589}$ (c=1, methanol)=−2

With a similar procedure as described in the example 12 the compounds 55, 56, 58, 60, 64 to 66 were prepared.

Example 13
a) Preparation of 5,6-dimethoxy-2-hydroxyimino-indanone 5,6-Dimethoxy-1-indanone (0.078 moles, 15 g) is dissolved in absolute ethanol (550 ml), thermostated at 50° C., and added with isoamyl nitrite (0.086 moles, 11.9 ml) and conc. HCl (11.9 ml). After a few minutes the product precipitates. The reaction is kept at 50° C. for further 3 hours, then cooled at r.t. and the solid is filtered washing with absolute ethanol (50 ml) and ethyl ether (100 ml). The product is dried in oven under vacuum at r.t. Yield: 16.3 g (94.4%)

b) Preparation of 5.6-dimethoxy-2-indanylamine

A solution of 5,6-dimethoxy-2-hydroxyimino-1-indanone (0.27 moles, 6 g) in glacial acetic acid (500 ml) is added with 96% sulfuric acid (3.3 ml) and 10% Pd/C (1.5 g). The mixture is hydrogenated in a Parr apparatus (r.t., 35 psi). When the hydrogen absorption ceases, the catalyst is filtered off through celite, washing with methanol (70 ml). The solution is evaporated to dryness, to obtain a white solid which is dissolved in water, then extracted with ethyl acetate (2×70 ml). The aqueous solution is alkalinized with a 1M sodium hydroxide solution to pH=8-8.5. The product is extracted with methylene chloride (2×70 ml). The organic solution is dried over sodium sulfate and evaporated under vacuum to obtain the solid product. Yield: 4.6 g (88.5%)

c) Preparation of 2-(5,6-dimethoxy-2-indanylamino)acetamide (CHF 3511)

5,6-Dimethoxy-2-indanylamine (0.024 moles, 4.6 g) and sodium bicarbonate (0.026 moles, 2.2 g) are added to a solution of chloroacetamide (0.024 moles, 2.2 g) in absolute ethanol (100 ml) and refluxed for 10 hours. The mixture is filtered at r.t. and the solution is evaporated to dryness. The resulting oil is chromatographed under medium pressure through silica gel (eluent: methylene chloride/methanol=90/10) Yield: 1.95 g (32.7%)—m.p.=135–138° C.

With a similar procedure as described in the example 13 the following compound were prepared:

2-(5-fluoro-2-indanylamino)acetamide hydrochloride (CHF 3480.01);

2-(5,6-difluoro-2-indanylamino)acetamide hydrochloride (CHF 3518.01).

In the subsequent Table 1, the abbreviations and structure formulae of the compounds of the examples as well as those of other compounds obtained with the same methods as above described are reported.

TABLE 1

α-Amino acids amides derivatives - Structure

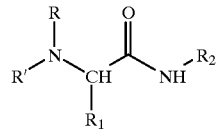

R' is H, if not otherwise precised.

| COMPOUND | R | R1 | R$_2$ | STEREO-CHEM | COMP. N. |
| --- | --- | --- | --- | --- | --- |
| CHF 2043 | (CH$_2$)$_6$CH$_3$ | CH$_2$OH | H | RS | 1 |
| CHF 2088 | (CH$_2$)$_4$CH$_3$ | CH$_2$OH | H | R | 2 |
| CHF 2102 | (CH$_2$)$_6$CH$_3$ | CH$_2$OH | H | R | 3 |
| CHF 2452.01 | (CH$_2$)$_4$CH$_3$ | CH$_2$OH | H | S | 4 |
| CHF 2525.01 | (CH$_2$)$_6$CH$_3$ | CH$_2$OH | H | S | 5 |
| CHF 2545 | CH(CH$_3$)$_2$ | CH$_2$OH | H | R | 6 |
| CHF 2560 | CH(CH$_3$)$_2$ | CH$_2$OH | H | S | 7 |
| CHF 2571 | (CH$_2$)$_6$CH$_3$ | CH$_2$C$_6$H$_5$ | H | RS | 8 |
| CHF 2583 | CH$_2$-cyclohexyl | CH$_2$OH | H | R | 9 |
| CHF 2597 | (CH$_2$)$_2$CH$_3$ | CH$_2$OH | H | S | 10 |
| CHF 2617 | (CH$_2$)$_6$CH$_3$ | CH$_2$OH | (CH$_2$)$_6$CH$_3$ | R | 11 |
| CHF 2621.01 | CH(CH$_3$)(CH$_2$)$_5$CH$_3$ | CH$_2$OH | H | R | 12 |
| CHF 2678 | (CH$_2$)$_2$C$_6$H$_5$ | CH$_2$OH | H | R | 13 |
| CHF 2679 | (CH$_2$)$_3$C$_6$H$_5$ | CH$_2$OH | H | R | 14 |
| CHF 2721 | (CH$_2$)$_5$CH$_3$ | CH$_2$OH | H | RS | 15 |
| CHF 2722 | (CH$_2$)$_7$CH$_3$ | CH$_2$OH | H | RS | 16 |
| CHF 2723 | (CH$_2$)$_8$CH$_3$ | CH$_2$OH | H | RS | 17 |
| CHF 2739.01 | CH$_2$—CH(CH$_3$)—CH(CH$_3$)—C$_2$H$_5$ | CH$_2$OH | H | RS | 18 |
| CHF 2750 | CH(CH$_2$)$_5$CH$_3$ / C$_2$H$_5$ | CH$_2$OH | H | RS RS | 19 |
| CHF 2751 | CH(CH$_2$)$_7$CH$_3$ / CH$_3$ | CH$_2$OH | H | RS RS | 20 |
| CHF 2768 | 1-(norbornyl-enyl)etyl | CH$_2$OH | H | RS endo | 21 |
| CHF 2769 | 1-(norbornyl-enyl)etyl | CH$_2$OH | H | RS exo | 22 |
| CHF 2803.01 | (CH$_2$)$_3$C$_6$H$_5$ | CH$_2$OH | H | S | 23 |
| CHF 2812 | (CH$_2$)$_3$C$_6$H$_5$ | CH$_2$OH | CH$_3$ | R | 24 |
| CHF 2818 | 1,2,3,4-tetra-hydro-2-naphthalenyl | CH$_2$OH | H | R RS | 25 |
| CHF 2824 | CH—(CH$_2$)$_2$C$_6$H$_5$ / CH$_3$ | CH$_2$OH | H | R RS | 26 |
| CHF 2847.01 | CH—CH$_2$C$_6$H$_5$ / CH3 | CH$_2$OH | H | R S | 27 |

TABLE 1-continued

α-Amino acids amides derivatives - Structure $$\begin{array}{c} R \quad\quad O \\ \diagdown N \diagup\diagdown \diagup R_2 \\ R' \diagup \quad CH \quad NH \\ \quad\quad | \\ \quad\quad R_1 \end{array}$$

R' is H, if not otherwise precised.

| COMPOUND | R | R1 | R$_2$ | STEREO-CHEM | COMP. N. |
|---|---|---|---|---|---|
| CHF 2865.01 | (CH$_2$)$_2$—CHC$_6$H$_5$ <br> \| <br> CH$_3$ | CH$_2$OH | H | R RS | 28 |
| CHF 2870.02 | CH(CH$_2$CH$_2$CH$_3$)$_2$ | CH$_2$OH | H | R | 29 |
| CHF 2880.01 | CH—C$_6$H$_5$ <br> \| <br> CH$_3$ | CH$_2$OH | H | R RS | 30 |
| CHF 2918 | (CH$_2$)$_4$—C$_6$H$_5$ | CH$_2$OH | H | R | 31 |
| CHF 2934.01 | 3-(4-methyl-)phenyl)propyl | CH$_2$OH | H | RS | 32 |
| CHF 2948.01 | 3-fluoro-phenyl)propyl | CH$_2$OH | H | RS | 33 |
| CHF 2967.01 | 3-(4-Chloro-phenyl)propyl | CH$_2$OH | H | RS | 34 |
| CHF 2968.01 | (CH$_2$)$_3$—C$_6$H$_5$ <br> R' = CH$_3$ | CH$_2$OH | H | RS | 35 |
| CHF 2982.01 | 1,2,3,4-tetra-hydro-2-naphtha-lenyl | CH$_2$OH | H | R R | 36 |
| CHF 2983.01 | 1,2,3,4-tetra-hydro-2-naphtha-lenyl | CH$_2$OH | H | R S | 37 |
| CHF 2990.01 | 1,2,3,4-tetra-hydro-2-naphtha-lenyl | CH$_2$OH | H | S S | 38 |
| CHF 2991 | 1,2,3,4-tetra-hydro-2-naphtha-lenyl | CH$_2$OH | H | S R | 39 |
| CHF 2993.01 | 2-indanyl | CH$_2$OH | H | S | 40 |
| CHF 2996 | " | CH$_2$OH | H | R | 41 |
| CHF 3009.01 | 1,2,3,4-tetra-hydro-2-naphtha-lenyl | CH$_3$ | H | S RS | 42 |
| CHF 3010.01 | 1,2,3,4-tetra-hydro-2-naphtha-lenyl | CH$_3$ | H | R RS | 43 |
| CHF 3011.01 | 2-naphtha-lenylmethyl- | CH$_2$OH | H | RS | 44 |
| CHF 3023.01 | (CH$_2$)$_3$—C$_6$H$_5$ | CH$_2$OAc | H | S | 45 |
| CHF 3066 | 6-Meo-1,2,3,4 tetrahydro-2-naphthalenyl | CH$_2$OH | H | R RS | 46 |
| CHF 3091.01 | 2-indanyl | CH$_3$ | H | RS | 47 |
| CHF 3107.01 | 3-(4-CF$_3$—phenyl)-propyl | CH$_2$OH | H | R | 48 |
| CHF 3145.01 | 1,2,3,4-tetra-hydro-2-naphthalenyl | CH$_2$OH | C$_6$H$_5$CH$_2$ | R RS | 49 |
| CHF 3186.01 | C$_6$H$_5$(CH$_2$)$_3$ | CH$_2$OH | C$_6$H$_5$CH$_2$ | R | 50 |
| CHF 3189.01 | C$_6$H$_5$(CH$_2$)$_3$ | CH$_2$OH | CH$_3$(CH$_2$)$_4$ | R | 51 |
| CHF 3195.01 | C$_6$H$_5$(CH$_2$)$_3$ <br> R' = C$_6$H$_5$—CH$_2$ | CH$_2$OH | H | R | 52 |
| CHF 3293 | (CH$_2$)$_3$—C$_6$H$_5$ <br> R' = n-butyl | CH$_2$OH | H | R | 53 |
| CHF 3381.01 | 2-indanyl | H | H | — | 54 |
| CHF 3394.01 | " | CH$_2$OH | CH$_3$ | R | 55 |
| CHF 3408.01 | " | H | CH$_3$ | — | 56 |
| CHF 3414.01 | 1,2,3,4-tetra-hydro-2-naphthalenyl | H | H | RS | 57 |
| CHF 3421.01 | 2-indanyl | CH$_3$ | CH$_3$ | R | 58 |

TABLE 1-continued

α-Amino acids amides derivatives - Structure $$\underset{R_1}{\overset{R}{\underset{|}{N}}}\text{—}\underset{|}{\overset{|}{CH}}\text{—}\overset{O}{\overset{\|}{C}}\text{—}NH\text{—}R_2$$

R' is H, if not otherwise precised.

| COMPOUND | R | R1 | R$_2$ | STEREO-CHEM | COMP. N. |
|---|---|---|---|---|---|
| CHF 3422.01 | " | CH$_2$OH | CH$_3$ | S | 59 |
| CHF 3427.01 | " | CH$_3$ | CH$_3$ | S | 60 |
| CHF 3431.01 | 2-indanyl | CH$_3$ | H | S | 61 |
| CHF 3434.01 | " | CH$_3$ | H | R | 62 |
| CHF 3440.01 | " R' = CH$_3$ | CH$_2$OH | H | R | 63 |
| CHF 3441.01 | 1,2,3,4-tetra-hydro-2-naphthalenyl | H | CH$_3$ | RS | 64 |
| CHF 3442.01 | 1,2,3,4-tetra-hydro-2-naphthalenyl | CH$_2$OH | CH$_3$ | R R | 65 |
| CHF 3443.01 | 1,2,3,4-tetra-hydro-2-naphthalenyl | CH$_2$OH | CH$_3$ | S R | 66 |
| CHF 3462.01 | 2-indanyl R' = CH$_3$ | CH$_2$OH | H | S | 67 |
| CHF 3480.01 | 5-F-2-indanyl | H | H | RS | 68 |
| CHF 3486.01 | 5-F-2-indanyl | CH$_2$OH | H | S RS | 69 |
| CHF 3488 | 2-indanyl R' = CH$_3$ | H | H | — | 70 |
| CHF 3511 | 5,6-MeO-2-indanyl | H | H | — | 71 |
| CHF 3512.01 | 5,6-MeO-2-indanyl | CH$_2$OH | H | S | 72 |
| CHF 3518.01 | 5,6-F-2-indanyl | H | H | — | 73 |
| CHF 3519.01 | 2-indanyl | CH$_2$OAc | H | S | 74 |
| CHF 3531.01 | 5-MeO-2-indanyl | H | H | RS | 75 |
| CHF 3539.01 | 5-MeO-2-indanyl | CH$_2$OH | H | S RS | 76 |
| CHF 3542.01 | 2-indanyl | CH$_2$OOC-iPr | H | S | 77 |
| CHF 3548.01 | " | CH$_2$OOC—C$_6$H$_5$ | H | S | 78 |

Anticonvulsant Activity

The compounds of the invention were evaluated in some pharmacological tests in order to investigate their potential anticonvulsant activity. To this end, compounds were screened in the maximal electroshock (MES) test. This model is widely used to assess the efficacy of antiepileptic agents against generalized and partial seizures. This study was performed in both rat and mouse by using the experimental procedure described in W. Löscher et al., Epilepsy Res., 2 (1988), 145–181. Briefly, a 60 Hz alternate current (mice 50 mA, rats 150 mA) was delivered for 0.2 sec through corneal electrods by means of an electrical stimulator. Anticonvulsant potency of a compound was determined after 60 min and up to 180 min from administration (p.o.) by calculation of its ED$_{50}$ for suppression of tonic hind limb extensions. Groups of 10 animals per dose were used and the ED$_{50}$ was calculated from the dose-effect curve accordingly to Litchfield and Wilcoxon (J. Pharmacol. Exp. Ther., 96 (1949), 99–113).

In the rat MES model only the time course of anticonvulsant activity was evaluated. Groups of 10 rats were treated at their equiactive dose 30, 60, 120, 240, 360 and 480 min before the establishment of the electroshock. The peak of anticonvulsant activity and the duration of action were then evaluated.

In another serie of experiments performed in mouse the neurotoxicity of the compounds was evaluated as a measure of the impaired motor function by using the horizontal screen test (L. L. Coughenour et al., Pharmacol. Bioch. and Behav., 6 (1977), 351–353). In this model mice are placed individually on top of a squire wire screen which is mounted horizontally on a metal rod, which is then rotated 180° so that mice are on the bottom of the screens. Impairment of the motor function is observed from the number of animals that falls from the screen or fail to climb to the top of the screens. The medial neurological toxic dose (TD$_{50}$) is than calculated as above. The ratio of TD$_{50}$ and ED$_{50}$ refers to the therapeutic index (T.I.) for each compound. The T.I. is used to show a useful separation between neurotoxicity and antiepileptic activity. The larger the T.I. would indicate a better separation between the above activities and a good profile as anticonvulsants.

In the mouse MES model all the examined compounds showed a potency of anticonvulsant activity expressed in moles better than that of milacemide and/or sodium valproate. The ED$_{50}$ values were comprised between 1.2 and 0.5 mmol/kg with a potency ratio ranging from 4.5 to 35 with respect to milacemide and from 1 to 6.7 with respect to sodium valproate.

The evaluation of the time course of anticonvulsant activity showed that some compounds were rapidly absorbed with a peak of the effect at 30 minutes after administration, whereas other compounds exerted more deferred effects that peaked even at three hours after administration.

A common feature to many compounds was a good persistence of the effects with a suppression of the convulsions equal to or greater than 50% still statistically significant more than three hours after administration.

The duration of action was longer than that of milacemide which was of about one hour.

The results of the MES test in mouse of the more representative compounds of the invention at 60 min after administration are shown in the following Table 2.

The activity of the compounds has been compared with that of two compounds of the prior art: FCE 28245, a prototype of a new serie of serine derivatives endowed with an anticonvulsant activity and TEVA compound 2 (a 1-aminoindane derivative), described in WO 94/22808 and in WO 95/18617 respectively.

| Compound (CHF) | $ED_{50}$ MES (mg/kg p.o.) | $TD_{50}$ Horizontal screen (mg/kg p.o.) | T.I. |
| --- | --- | --- | --- |
| 2993 | 44 | 1172 | 27 |
| 2996 | 34 | >1500 | 44 |
| 2983 | 43 | 1300 | 30 |
| 2991 | 38 | 1099 | 29 |
| 3431 | 22 | 251 | 11 |
| 3440 | 35 | 689 | 20 |
| 3381 | 21 | 274 | 13 |
| FCE 28245 | 180 | 1670 | 9 |
| TEVA Comp. 2 | 38 | 299 | 8 |

T.I.: therapeutic index

All compounds were administered as HCl salts. The individual enantiomers of 2-aminoindane and aminotetraline derivatives showed a significant anticonvulsant activity. The (S)-hydroxyl-2 aminoindane derivative CHF2993 and its enantiomer (R) CHF2996 were equipotent in the MES test. This latter compound showed also the higher T.I. (44) since its low value of neurotoxicity (>1500 mg/kg p.o.). The introduction of a methyl-group in the moiety of the CHF2993 resulted in a compound (CHEF3440) with the same anticonvulsant activity but with an increase of the neurotoxicity ($TD_{50}$=689). Conversely, both the (S) 2-(2-indanylamino)propionamide and the 2-(2-indanylamino) acetamide derivatives CHF3431 and CHF3381 were more potent in inhibiting MES but resulted more neurotoxic that the previously mentioned compounds. A good profile of anticonvulsant activity was also observed with the 3-hydroxy-2-tetralinamine derivatives CHF2983 (R,S enantiomer) and CHF2991 (S,R enantiomer).

All the tested compounds were about 3–4 times more potent than FCE28245, chemically 3-hydroxy-2-(4-(3-phenylpropyloxy)benzylamino)propanamide methane-sulphonate.

It is also worth noting that the 2-aminoindane derivative CHF3381 had a higher T.I. than the prior art 1-aminoindane compound 2 known from WO 95/18617, chemically (S)-2-(indanylamino)acetamide. In fact the 2-aminoindane compound of the invention was more potent as an anticonvulsant than the 1-aminoindane of the prior art. Taken together these results it appears that the class of the 2-aminoindane compounds of the invention exhibited less impairment of the motor coordination than the compound of the prior art.

Further to the MES test in mouse, some compounds were also evaluated in the MES test in rat and in a chemical model of tonic convulsions induced by bicuculline accordingly to the procedure described in Swinyard E. A. et al., Antiepileptic Drugs, 3$^{rd}$ Edition, Raven Press, New York (1989). In this model mice were observed for 30 minutes after administration of a dose of bicuculline (s.c.) that induced in 97% of the animals a presence of tonic convulsions. In animals treated with compounds, abolition of the hindleg tonic-extension component is taken as the end point thus suggesting that the substance under examination has the ability to prevent the seizure spread.

As reference compound FCE 26743 (S)-2-(4-(3-fluorobenzyloxy)benzylamino)pro panamide was used, disclosed in the prior art in EP-B1-0400495.

The results are shown in Table 3 as follows:

| Compound (CHF) | $ED_{50}$MES (MG/KG P.O.) | Peak of activity (hrs)* | Duration of action (hrs)** | $ED_{50}$ bicuculline mouse (mg/kg p.o) |
| --- | --- | --- | --- | --- |
| 2993 | 31 | 3 | 6 | 65 |
| 2996 | 32 | 1 | 2 | n.t. |
| 2983 | 19 | 1 | 2 | 62 |
| FCE 26743 | 11 | 0.5 | 1 | 20 |

*: time of the maximal effect
**: time at which the protection is statistically significant
n.t.: not tested In the rat MES test CHF2993, CHF2996 and FCE 26743 showed an anticonvulsant activity close to that found in the same model in mouse. In this test CHF 2983 was more potent, with an $ED_{50}$ of 19 mg/kg p.o., lower than that reported in mouse MES. The analysis of the kinetics of the pharmacological effects showed that CHF2993 had the longest duration of action (6 hours). In any case the duration of action of all the tested compounds was longer than that of the reference compound FCE 26743 (1 hour). In the bicuculline-induced convulsions in mice, $ED_{50}$ for CHF2993, CHF2983 and FCE 26743 was 65, 62 and 20 mg/kg p.o., respectively. Although these values were higher than those obtained in mouse MES test, still these values were in the same order of potency of their MES anticonvulsant activity.

Taken together these results, we can conclude that the compounds described herein showed a significant anticonvulsant activity in the MES model in both mouse and rat and also in a model of bicuculline-induced convulsions in mouse. The activity exhibited by these compounds in mice were almost similar to that found for some standard antiepileptic drugs including phenytoin, carbamazepine, and at least four times higher than sodium valproate, compounds for which literature data evidentiate smaller therapeutic indexes in comparison with those found in the present investigation.

The compounds of the invention can be administered in a variety of dosage forms, e.g. orally, in the form of tablets, capsules, sugar or film coated tablets, liquid solutions; rectally, in the form of suppositories, parenterally, e.g. intramuscularly or by intravenous or injection or infusion. The therapeutic regimen for the different clinical syndromes must be adapted to the type of pathology taking into account as usual, also the route of administration, the form in which the compound is administered and the age, weight and conditions of the subject involved.

In an embodiment the therapeutically effective amount is from about 1 mg to about 1000 mg, preferably from about 10 mg to about 300 mg.

Of course, these dosage regimens may be adjusted to provide the optimal therapeutic response.

The nature of pharmaceutical compositions containing the compounds of this invention in association with pharmaceutically acceptable carriers or diluents will, of course, depend upon the desired route of administration.

The compositions may be formulated in the conventional manner with the usual ingredients. For example, the compounds of the invention may be administered in the form of aqueous or oily solutions or suspensions, tablets, pills, gelatine capsules, syrups, drops or suppositories.

Thus, for oral administration, the pharmaceutical compositions containing the compounds of this invention are preferably tablets, pills or gelatine which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or they may also contain binders, such as starches, gelatine, methylcellulose, carboxymethylcellulose, gum arabic, tragacanth, polyvinylpyrrolidone; disaggregating agents, such as starches, alginic acid, alginates, sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol. The suspension and the emulsions may is contain as carrier, for example, a natural gum, agar, sodium alginate, pectin, methylcellulose, carboxymethylcellulose, or polyvinyl alcohol. The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusion may contain as carrier, for example, sterile water or preferably they may be in the form of sterile aqueous isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

What is claimed is:

1. A compound of formula I

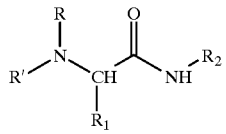

(I)

wherein:

R is 1,2,3,4-tetrahydro-2-naphthalenyl or 2-indanyl optionally substituted with alkyl, alkoxy, halogen or haloalkyl;

R' is hydrogen; alkyl; phenyl; phenylalkyl;

$R_1$ is hydrogen, $C_1$–$C_4$ alkyl, optionally acylated $C_1$–$C_4$ hydroxyalkyl or phenylalkyl;

$R_2$ is hydrogen; alkyl; phenyl; phenylalkyl.

2. The compound according to claim 1 wherein:

$R_1$ is $CH_2OH$; R is [$C_3$–$C_{10}$ alkyl, phenyl-($C_2$–$C_4$)-alkyl, or] 1,2,3,4-tetrahydro-2-naphthalenyl or 2-indanyl optionally substituted with alkyl, alkoxy, halogen or haloalkyl; R' is hydrogen or methyl and $R_2$ is hydrogen.

3. The compound according to claim 1 wherein $R_1$ is hydrogen or methyl, R is 1-,2,3,4-tetrahydro-2-naphthalenyl or 2-indanyl optionally substituted with alkyl, alkoxy, halogen or haloalkyl and R' and $R_2$ are hydrogen.

4. The compound according to claim 1 wherein $R_1$ is $CH_2OH$;

R is [phenyl-($C_2$–$C_3$)-alkyl,] 1,2,3,4-tetrahydro-2-naphthalenyl, 2-indanyl; R' and $R_2$ are hydrogen.

5. A process for the preparation of the compounds of claim 1, comprising reacting amino acids esters or amides of formula II

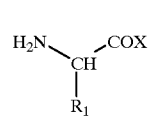

(II)

wherein $R_1$ is as defined above and X is an alkoxy group or a $NHR_2$ group, wherein $R_2$ is as defined above, with compounds of formula III

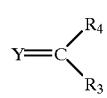

(III)

wherein Y is an oxygen atom or a NH group, whereas $R_3$ and $R_4$, together with the carbon atom they are linked to, form one of the groups R or R', as defined above, to give compounds of formula IV

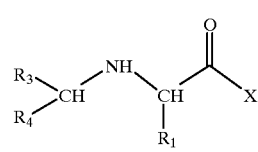

(IV)

which can then be transformed into compounds of formula I by means of one or more of the following reactions:

when X is an alkoxy group, reaction with an amine of formula $R_2$—$NH_2$;

N-alkylation;

acylation of any hydroxy group present in $R_1$;

salification and/or optical resolution, elimination of any protecting groups.

6. A process for the preparation of the compound of claim 1, comprising condensing an alfahalogen ester of formula V

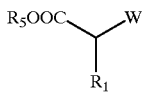

(V)

wherein $R_1$ is as defined above and preferably H, W is a halogen atom and $R_5$ is an alkyl group, with an amine of formula VI

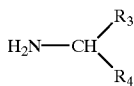

(VI)

wherein $R_3$ and $R_4$ are as defined above, and subsequent amidation with the amine $R_2$—$NH_2$ wherein $R_2$ is as defined above to give compounds of formula (I).

7. A pharmaceutical composition comprising the compound of claim 1 in admixture with suitable excipients or carriers.

8. A method of treating neurodegenerative disease, comprising administering an effective amount of the compound of claim 1 to a patient in need thereof.

9. A method of treating neurodegenerative disease, comprising administering an effective amount of the compound of claim 2 to a patient in need thereof.

10. A method of treating neurodegenerative disease, comprising administering an effective amount of the compound of claim 3 to a patient in need thereof.

11. A method of treating neurodegenerative disease, comprising administering an effective amount of the compound of claim 4 to a patient in need thereof.

12. A method of treating neurodegenerative disease, comprising administering an effective amount of the compound of claim 5 to a patient in need thereof.

13. The process of claim 6, wherein W is a chlorine or bromine.

14. A method of treating neurodegenerative disease, comprising administering an effective amount of the pharmaceutical composition of claim 7 to a patient in need thereof.

\* \* \* \* \*

UNITED STATES PATENT AND TRADEMARK OFFICE
CERTIFICATE OF CORRECTION

PATENT NO. : 6,114,391
DATED : September 5, 2000
INVENTOR(S) : Paolo Chiesi, et al.

It is certified that error appears in the above-identified patent and that said Letters Patent is hereby corrected as shown below:

Title page,
Item [86], PCT information is incorrectly listed. Item [86] should read as follows:

[86] PCT No.: PCT/EP97/03773
§ 371 Date: Feb. 18, 1999
§ 102(e) Date: Feb. 18, 1999

Signed and Sealed this

Eighteenth Day of September, 2001

Attest:

NICHOLAS P. GODICI
Attesting Officer   Acting Director of the United States Patent and Trademark Office

UNITED STATES PATENT AND TRADEMARK OFFICE
CERTIFICATE OF CORRECTION

PATENT NO.    : 6,114,391
DATED         : September 5, 2000
INVENTOR(S)   : Paolo Chiesi et al.

It is certified that error appears in the above-identified patent and that said Letters Patent is hereby corrected as shown below:

Column 20,
Lines 7 and 8, should read -- is $CH_2OH$; R is 1,2,3,4-tetrahydro-2-naphthalenyl or 2-indanyl --;
Line 18, should read -- R is 1,2,3,4-tetrahydro-2- --.

Signed and Sealed this

Twentieth Day of August, 2002

Attest:

Attesting Officer

JAMES E. ROGAN
Director of the United States Patent and Trademark Office